United States Patent [19]
Okazaki

[11] Patent Number: 5,614,067
[45] Date of Patent: Mar. 25, 1997

[54] LEACHING DEVICE FOR ELECTROLYZED SILVER

[75] Inventor: Tatsuo Okazaki, Kamifukuoka, Japan

[73] Assignee: OMCO Co., Ltd., Iruma-gun, Japan

[21] Appl. No.: 568,116

[22] Filed: Dec. 6, 1995

[30] Foreign Application Priority Data

Dec. 7, 1994 [JP] Japan .................................. 6-331278

[51] Int. Cl.⁶ ............................................. C25C 7/00
[52] U.S. Cl. ..................... 204/228; 204/292; 204/229; 204/233
[58] Field of Search .................................. 204/228, 229, 204/401–402, 406, 409, 292, 233

[56] References Cited

U.S. PATENT DOCUMENTS 3,865,710  2/1975  Phipps ........................................ 204/228
3,936,364  2/1976  Middle ...................................... 204/228 X
4,769,119  9/1988  Grundler ................................... 204/228 X
4,936,979  6/1990  Brown ....................................... 204/228 X Primary Examiner—Donald R. Valentine
Attorney, Agent, or Firm—Armstrong, Westerman, Hattori, McLeland, & Naughton

[57] ABSTRACT

A leaching device for electrolyzed silver comprising a pair of silver electrodes an electrolysis power source for applying a DC electrolyzing voltage between both of the electrodes, a power source control circuit for ON/OFF control of the electrolysis power source, a current control circuit for controlling the electrolyzing current flowing between both of the electrodes thereby controlling the leaching amount of silver, a polarity switching circuit for switching the polarity of the electrolyzing voltage, a driving circuit for driving the polarity switching circuit, and an abnormality sensing circuit that senses the abnormality of the silver electrode based on the change of an electric current flowing to the silver electrode.

5 Claims, 3 Drawing Sheets

LEACHING DEVICE FOR ELECTROLYZED SILVER

BACKGROUND OF THE INVENTION

1. Field of the Invention

The present invention concerns a leaching device for electrolyzed silver for preparing silver ion-sterilized water by leaching silver ions into water and, particularly, it relates to a leaching device for electrolyzed silver capable of detecting abnormality such as cutting or thinning of a silver electrode by dissolution.

2. Description of the Prior Art

A leaching device for electrolyzed silver has been generally known in which a pair of silver electrodes made of a material leaching silver into water when used as an anode (silver, silver alloy or the like) and the polarity of an electrolyzing voltage is periodically switched for hindering deposition of calcium or the like to the electrodes.

During continuous electrolysis in such an electrolyzed silver dissolving device, the silver electrode is gradually thinned and then eliminated completely since silver ions are leached from the silver electrode into water.

However, since the leaching devices for electrolyzed silver of the prior art have no means for detecting abnormality such as cutting and dissolution of the silver electrode, they involve a problem of over looking such a trouble of the device that Silver ion sterilized water can no more be obtained even if the leaching device for electrolyzed silver is operated.

As a countermeasure for solving the problem, periodical exchange of the silver electrodes may be considered. However, since the leaching amount of silver varies depending on the electrolyzing current, this method involves a problem that the silver electrodes can not be exchanged at an optimum timing.

OBJECT OF THE INVENTION

The present invention has been achieved in view of the foregoing situations and it is an object thereof to provide a leaching device for electrolyzed silver capable of reliably detecting abnormality of a silver electrode thereby exchanging the silver electrode at an optimum timing.

Another object of the present invention is to provide a leaching device for electrolyzed silver capable of operating the device only when silver ion sterilized water is required.

A further object of the present invention is to provide a leaching device for electrolyzed silver capable of keeping the leaching amount of silver constant.

A further object of the present invention is to provide a leaching device for electrolyzed silver capable of keeping a silver concentration in silver ion sterilized water content.

A further object of the present invention is to provide a leaching device for electrolyzed silver capable of easily switching polarity.

A further object of the present invention is to provide a leaching device for electrolyzed silver capable off constituting an abnormal sensing circuit by a simple circuit structure.

A still further object of the present invention is to provide a leaching device for electrolyzed silver capable of constituting an abnormal sensing circuit at a high accuracy.

SUMMARY OF THE INVENTION

The foregoing objects can be attained in accordance with the present invention by a leaching device for electroyzed silver comprising:

- a pair of silver electrodes;
- an electrolysis power source for applying a DC electroyzing voltage between both of the electrodes;
- a power source control circuit for ON/OFF control of the electrolysis power source;
- a current control circuit for controlling an electrolyzing current flowing between both of the electrodes thereby controlling the leaching amount of silver;
- a polarity switching circuit for switching the polarity of the electrolyzing voltage;
- a driving circuit for driving the polarity switching circuit; and
- an abnormality sensing circuit that senses the abnormality of the silver electrode based on the change of an electric current flowing to the silver electrode.

In a preferred embodiment of the present invention, the power source control circuit comprises a detection circuit for detecting the flow of feed water or silver ion sterilized water thereby applying ON/OFF control to the electrolysis power source.

In another preferred embodiment of the present invention, the current control circuit comprises a constant current circuit.

In a further preferred embodiment according to the present invention, the current control circuit comprises a circuit for controlling the electrolyzing current depending on the flow rate of feed water or silver sterilized water.

In a further preferred embodiment according to the present invention, the driving circuit comprises a timer circuit for driving the polarity switching circuit on every predetermined time interval.

In a further preferred embodiment according to the present invention, the abnormality sensing circuit comprises a circuit for sensing the abnormality when the electrolyzing current lowers to less than an allowable value.

In a further still preferred embodiment according to the present invention, the abnormality sensing circuit comprises a circuit both terminals of which are connected respectively with opposed ends of the anode and which senses the abnormality when the electrolyzing current flowing between the opposed ends of the anode lowers to less than an allowable value.

In accordance with the present invention, an abnormality sensing circuit is incorporated in the device for sensing the abnormality of the silver electrode based on the change of the current flowing to the silver electrode. Therefore, it is possible to reliably detect the abnormality of the silver electrode and exchange the silver electrode at an optimum timing. As a result, the device is quite free from such a disadvantage as over looking the state not capable of obtaining an aimed silver ion sterilized water from an electrolysis vessel.

Further, in accordance with the present invention, a current control circuit comprises a detection circuit for detecting the flow of feed water or silver ion sterilized water thereby applying ON/OFF control to the electrolysis power source. Therefore, it is possible to operate the device only when the silver ion sterilized water is required.

Further, in accordance with the present invention, the current control circuit comprises a constant current circuit. Therefore, it is possible to keep the leaching amount of the silver constant.

Further, in accordance with the present invention, the current control circuit comprises a circuit of controlling the electrolyzing current depending on the flow rate of feed water or silver ion sterilized water. Therefore, it is possible to keep the silver ion concentration of silver ion sterilized water constant.

Further, in accordance with the present invention, a driving circuit comprises a timer circuit for driving a polarity switching circuit on every predetermined time interval. Accordingly, polarity switching can be automated.

Further, in accordance with the present invention, an abnormality sensing circuit comprises a circuit that senses the abnormality when an electrolyzing current lowers to less than an allowable value. Therefore, it is possible to constitute the abnormality sensing circuit with a simple circuit structure.

Further, in accordance with the present invention, the abnormality sensing circuit comprises a circuit both terminals of which are connected respectively with opposed ends of the anode and which senses the abnormality when the electrolyzing current flowing between the opposed ends of the anode lowers to less than an allowable value. Therefore, it is possible to further improve the accuracy by direct detection for the consumed state of the anode.

BRIEF DESCRIPTION OF ACCOMPANYING DRAWINGS

The present invention will be explained more specifically with reference to the accompanying drawings, wherein FIG. 1 is a circuit diagram showing a leaching device for electrolyzed silver in a first embodiment according to the present invention;

FIG. 2 is a circuit diagram showing a leaching device for electrolyzed silver in a second embodiment according to the present invention; and FIG. 3(a) is an explanatory view for illustrating problems in a case of mounting a silver electrode to an electrolysis vessel and FIGS. 3(b) and (c) are explanatory views showing the method of solving the problem, respectively.

DESCRIPTION OF THE PREFERRED EMBODIMENTS

The present invention will be explained with reference to the drawings.

Figure 1:
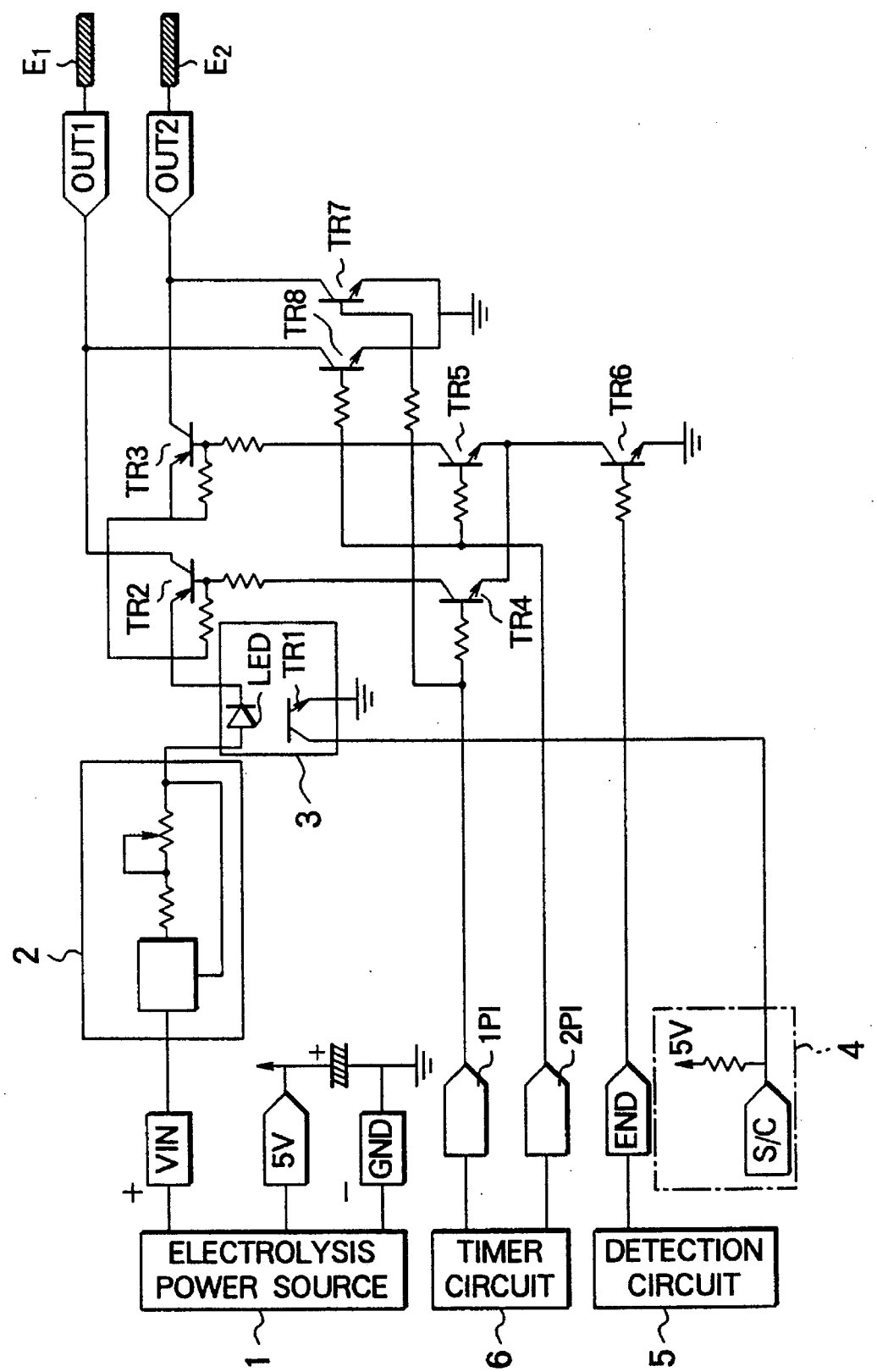

FIG. 1 shows a leaching device for electrolyzed silver in a first embodiment according to the present invention. In the drawing, a DC electrolyzed voltage from an electrolysis power source 1 is applied between a pair of silver electrodes $E_1$ and $E_2$.

As shown in FIG. 1, a constant current circuit 2, a current detection circuit 3 comprising a phototransistor $TR_1$ and a light emitting diode LED, a transistor $TR_2$ and a transistor $TR_3$ are connected between the electrolysis power source 1 and each of the silver electrodes $E_1$ and $E_2$. The collector of the phototransistor $TR_1$ is connected to an abnormality sensing circuit 4 for sensing the abnormality of the silver electrodes $E_1$, $E_2$.

As shown in FIG. 1, a collector of a transistor $TR_4$ is connected with the base of the transistor $TR_2$, while a collector of a transistor $TR_5$ is connected with the base of the transistor $TR_3$. Further, emitters of both of the transistors $TR_4$ and $TR_5$ are connected with a collector of an emitter-grounded transistor $TR_6$.

As shown in FIG. 1, the base of the transistor $TR_6$ is connected with a detection circuit 5 for detecting the flow of feed water to be supplied to an electrolysis vessel (not illustrated) or the flow of a silver ion sterilized water delivered from the electrolysis vessel thereby outputting an electrolysis ON/OFF control signal, so that the transistor $TR_6$ is turned ON upon output of the electrolysis ON/OFF control signal from the detection circuit 5.

As shown in FIG. 1, each of the bases of the transistor $TR_4$ and $TR_5$ is connected with a timer circuit 6 for supplying a current alternately to terminals 1PI, 2PI on every predetermined time interval in such a way that the transistor $TR_4$ turns ON when the current flows to the terminal 1PI, while the transistor $TR_5$ turns ON when the current flows to the terminal 2PI.

Also as shown in FIG. 1, the base of the transistor $TR_4$ is connected with the base of an emitter-grounded transistor $TR_7$, and the base of the transistor $TR_5$ is connected with the base of an emitter-grounded transistor $TR_8$. The collectors of the transistors $TR_7$, $TR_8$ are connected, respectively, to the collectors of the transistors $TR_3$, $TR_2$.

Operation of this embodiment will be explained.

At the initial state, all of the transistors $TR_1$, $TR_2$, $TR_3$, $TR_4$, $TR_5$, $TR_6$, $TR_7$ and $TR_8$ are kept OFF and, accordingly, electrolyzing voltage is not applied in this state between both of the silver electrodes $E_1$ and $E_2$.

In this state, when the detection circuit 5 detects the flow of feed water or silver ion sterilized water, the detection circuit 5 outputs an electrolysis ON/OFF control signal to the base of the transistor $TR_6$ to turn the transistor $TR_6$ to ON.

In this instance, when a current is supplied from the timer circuit 6 to the terminal 1PI, the transistors $TR_2$, $TR_4$ and $TR_7$ turn OFF. Accordingly, the electrolyzing current from the electrolysis power source 1 flows by way of the constant current circuit 2, the light emitting diode LED, the transistor $TR_2$, the silver electrode $E_1$, tile silver electrode $E_2$ and the transistor $TR_7$ and an electrolyzing voltage is applied between both of the silver electrodes $E_1$ and $E_2$ with the silver electrode $E_1$ as an anode and the silver electrode $E_2$ as a cathode.

On the other hand, when a current is supplied from the timer circuit 6 to the terminal 2PI, the transistors $TR_2$, $TR_5$ and $TR_8$ turn ON. Accordingly, the electrolyzed current from the electrolysis power source 1 flows by way of the constant circuit 2, the light emitting diode LED, the transistor $TR_3$, the silver electrode $E_2$, the silver electrode $E_1$, and the transistor $TR_8$, and an electrolyzing voltage is applied between both of the silver electrodes $E_2$ and $E_2$ with the silver electrode $E_2$ as an anode and the silver electrode $E_1$ as a cathode. That is, the polarity of the silver electrodes $E_1$, $E_2$ is inverted.

By the way, if the polarity is switched instantaneously, short circuit may sometimes be caused by a time lag of signal to each of the electrodes and a delay of current switching time, so that it is desirable to apply a current of an opposite polarity with a predetermined time interval upon switching of the polarity as is well-known.

Further, when a great amount of electrolyzed water is formed by an electrolyzing operation for once, it is preferred to switch the polarity by the above-mentioned method on every predetermined period of electrolysis accumulation time even during use. Further, in a case where the amount of use for once is small, it is preferred that the polarity is not switched during use of electrolyzing device but the polarity is switched after the elapse of a predetermined period of accumulation and the use of electrolysis device is stopped, whereby a current of an opposite polarity is applied to the electrode always switched for the polarity upon starting the next electrolysis operation.

By the way, when the electrolyzing current flows to the light emitting diode LED, the phototransistor $TR_1$ turns ON and the abnormality detection circuit 4 is grounded to the earth by way of the phototransistor $TR_1$. Therefore, the output from the abnormality sensing circuit 4 lowers to 0 V to sense the absence of abnormality for the silver electrode $E_1$, $E_2$.

When silver ions are leached into water of an electrolysis vessel not illustrated to prepare silver ion sterilized water, the silver electrode $E_1$ or $E_2$ on the side of the anode is gradually consumed and then finally eliminated completely. Then, the electrolyzing current flows no more, by which the light emitting diode LED in the current detection circuit 3 is distinguished to turn the phototransistor $TR_1$ to OFF. Therefore, the output of the abnormality sensing circuit 4 increases to 5 V to sense the abnormality of the silver electrode $E_1$ or $E_2$.

Then, since the abnormality of the silver electrode $E_1$, $E_2$ can be detected reliably, the silver electrode $E_1$, $E_2$ can be exchanged at an optimum timing. Further, since the electrolysis is controlled to ON/OFF by the signal from the detection circuit 5 that detects the flow of the silver ion sterilized water, the electrolyzing voltage can be applied between the silver electrodes $E_1$ and $E_2$ only when silver ion sterilized water is required. Further, the electrolyzing current is kept constant by the constant current circuit 2 thereby making the leaching amount silver $E_{20}$ constant. Further, since the abnormality of the silver electrode $E_1$, $E_2$ can be sensed by the simple current detection circuit 3 comprising the light emitting diode LED and the phototransistor $TR_1$, the circuit structure can be simplified.

Figure 2:
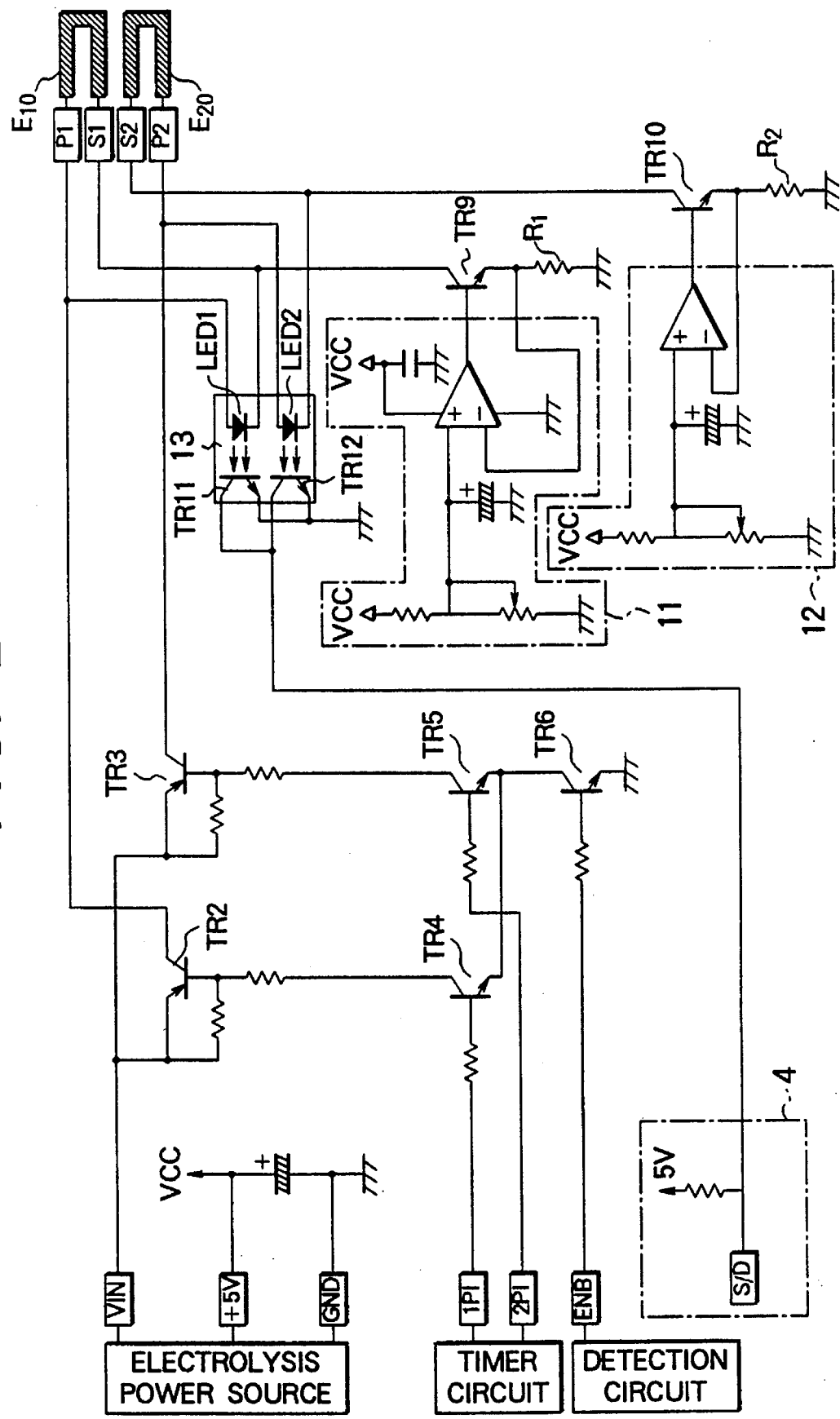

FIG. 2 illustrates a second embodiment of the present invention which is to be explained. Components or portions identical with those in FIG. 1 carry the same reference numerals for which detailed explanations will be omitted.

In FIG. 2, each of a pair of silver electrodes $E_{10}$, $E_{20}$ each of a U-shaped configuration having opposed leg ends, and leg ends P1, P2 on one side of the silver electrodes $E_{10}$, $E_{20}$ are connected, respectively, by way of transistors $TR_2$, $TR_3$ to an electrolysis power source 1, while leg ends $S_1$, $S_2$ on the other side of the electrodes $E_{10}$, $E_{20}$ are connected to collectors of emitter-grounded transistors $TR_9$ and $TR_{10}$ respectively. Further, a constant current is always inputted from each of constant current circuits 11, 12 to the base for each of the transistors $TR_9$, $TR_{10}$ and, accordingly, each of the transistors $TR_9$, $TR_{10}$ is always kept ON.

In FIG. 2, a current detection circuit 13 comprises a light emitting diode $LED_1$ both terminals of which are connected respectively with opposed leg ends P1, S1 of the silver electrode $E_{10}$, a light emitting diode $LED_2$ both terminals of which are connected respectively with opposed leg ends P2, S2 of the silver electrode $E_{20}$, and emitter-grounded phototransistors $TR_{11}$, $TR_{12}$ corresponding to the light emitting diodes $LED_1$, $LED_2$ respectively. Collectors of both of the phototransistors $TR_{11}$ and $TR_{12}$ are connected to an abnormality sensing circuit 4.

The operation of this preferred embodiment is to be explained.

For instance, in a case of using the silver electrode $E_{10}$ as an anode and the silver electrode $E_{20}$ as a cathode, an electrolyzing current from the electrolysis power source 1 flows through the transistor $TR_2$, the silver electrode $E_{10}$, the silver electrode $E_{20}$, and the transistor $TR_{10}$, in which the current value is controlled by changing a setting value to the constant current circuit 12. In this case, since a resistor $R_1$ is connected to the emitter of the transistor $TR_9$, the electrolyzing current does not flow by way of the leg end S1 to the transistor $TR_9$, so that both terminals of the light emitting diode $LED_2$ are at an identical potential.

On the other hand, in a case of using the silver electrode $E_{20}$ as the anode and the silver electrode $E_{10}$ as the cathode, the electrolyzing current from the electrolysis power source 1 flows by way of the transistor $TR_3$, the silver electrode $E_{20}$, the silver electrode $E_{10}$ and the transistor $TR_9$, in which the current value is controlled by changing a setting value to the constant current circuit 11. In this case, since a resistor $R_2$ is connected to the emitter of the transistor $TR_{10}$, the electrolyzing current does not flow by way of the leg end S2 to the transistor $TR_{10}$, and both sides of the light emitting diode $LED_2$ are at an identical potential.

In a case of using the silver electrode $E_{10}$ as the anode and the silver electrode $E_{20}$ as the cathode, if the silver electrode $E_{10}$ is consumed by the leaching of the silver ions and is cut at a midway portion between opposed ends $P_1$ and $S_1$, a potential difference is caused between opposed leg ends $P_1$ and $S_1$, which were at an identical potential. Therefore, a portion of the electrolyzing current flows through the light emitting diode $LED_1$ and the transistor $TR_9$, by which the light emitting diode $LED_1$ is lit to turn the phototransistor $TR_{11}$ to ON. Therefore, the output of the abnormality sensing circuit 4 usually indicating 5 V is lowered to 0 V, by which the abnormality of the silver electrode $E_{10}$ is sensed. Also in a case of using the silver electrode $E_{20}$ as the anode, the operation is similar and the abnormality of the silver electrode is sensed by the abnormality sensing circuit 4.

Then, in the case of this embodiment just described above, since the cutting of the silver electrode $E_{10}$, $E_{20}$ can be detected directly, the detection accuracy can be improved further compared with the case of the first embodiment.

In both of the preferred embodiments described above, explanation has been made to a case of controlling the electrolyzing current constant by the constant current circuit 2, 11 or 12, but the variable resistor portion may be changed in accordance with the flow rate of feed water or silver ion sterilized water to control the leaching amount of silver. This can always keep the silver concentration constant in the silver ion sterilized water even when the flow rate of the feed water or silver ion sterilized water varies.

Further, in both of the preferred embodiments, explanation has been made to a case of switching the polarity of the silver electrodes $E_1$, $E_2$ or $E_{10}$, $E_{20}$ on every predetermined time interval by using the timer circuit 6. Alternatively, an accumulation meter for accumulating the current to both of the electrodes may be disposed and the polarity switching is conducted on every time when the accumulated value reaches a setting value.

Further, in both of the preferred embodiments described above, explanation has been made to a case of ON/OFF control for electrolysis by a signal from the detection circuit 5 for detecting the flow of feed water or silver ion sterilized water. However, in a system, for example, of preparing silver ion sterilized water by utilizing midnight power and storing the prepared water in a tank, the electrolysis ON/OFF may also be controlled by using a timer.

Figure 3A:
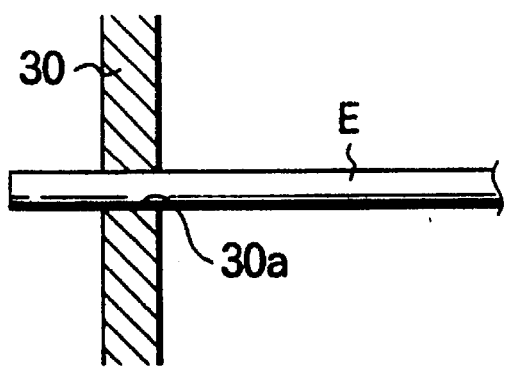

Although not explained particularly for both of the preferred embodiments described above, in a case, for example, as shown in FIG. 3(a) in which the silver electrode E is merely inserted into a hole 30a formed to a side wall of an electrolysis cell 30, there is a worry that silver ion sterilized water may possibly be leaked from the aperture 30a to the outside of the electrolysis vessel 30.

Figure 3B:
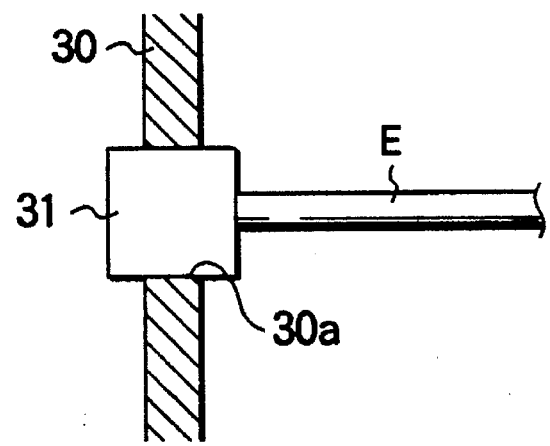
Figure 3C:
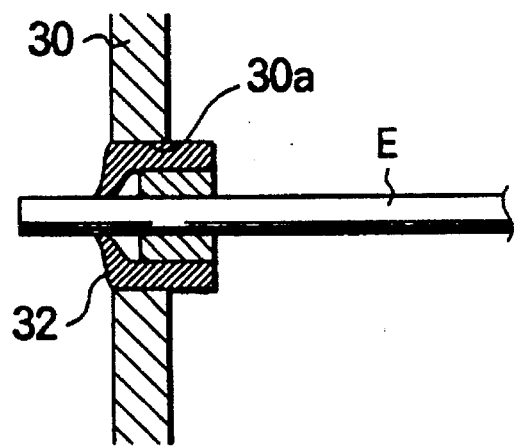

For a countermeasure in such a case as shown, for example, in FIG. 3(b), a plug 31 such as made of titanium is press fit into the aperture 30a and the silver electrode E is attached to the plug 31 or as shown in FIG. 3(c), a seal member 32 such as made of rubber may be disposed in the aperture 30a and the silver electrode E is penetrated through the seal member 32, so that the aperture 30a can be closed by the seal member 32 if the silver electrode E is consumed or eliminated.

As has been described above, according to the present invention, since the abnormality sensing circuit is disposed for sensing the abnormality of the silver electrode based on the change of the current flowing to the silver electrode, it is possible to reliably detect the abnormality of the silver electrode and exchange the silver electrode at an optimum timing. Therefore, the present invention is quite free from such a disadvantage as overlooking an undesired state in which no aimed sterilized water is formed from the electrolysis vessel.

Further, according to the present invention, since the power source control circuit comprises the detection circuit for detecting the flow of feed water or silver ion sterilized water thereby applying ON/OFF control to the electrolysis power source, the device can be operated only when silver ion sterilized water is required.

Further, according to the present invention, since the electric current control circuit comprises the constant current circuit, the leaching amount of silver can be kept constant.

Further, according to the present invention, since the electric current control circuit comprises a circuit of controlling the electrolyzing current depending on the flow rate of feed water or silver ion sterilized water, the silver concentration in the silver ion sterilized water can always be kept constant even if the flow rate of the feed water or the like varies.

Further, according to the present invention, since the driving circuit comprises the timer circuit for driving the polarity switching circuit on every predetermined time interval, the polarity can be switched easily and deposition of calcium to the electrode can be prevented.

Further, according to the present invention, since the abnormality sensing circuit comprises a circuit for sensing abnormality when the electrolyzing current lowers to less than an allowable value, the abnormality sensing circuit can be constituted with a simple circuit structure.

Further, according to the present invention, since the abnormality sensing circuit comprises a circuit both terminals of which are connected respectively with opposed ends of the anode and which detects the abnormality when the electrolyzing current flowing between the opposed ends of the anode lowers to less than an allowable value, detection accuracy can be improved further by direct detection for the consumed state of the anode.

What is claimed is:

1. A leaching device for electrolyzed silver comprising:
   a pair of silver electrodes which form an anode and a cathode;
   an electrolysis power source for applying a DC electrolyzing voltage between both of the electrodes;
   a power source control circuit for ON/OFF control of the electrolysis power source;
   a current control circuit for controlling the electrolyzing current flowing between both of the electrodes thereby controlling the leaching amount of the silver;
   a polarity switching circuit for switching the polarity of the electrolyzing voltage;
   a driving circuit for driving the polarity switching circuit; and
   an abnormality sensing circuit that senses the abnormality of the silver electrode based on the change of an electric current flowing to the silver electrode, said abnormality sensing circuit comprising a circuit both terminals of which are connected respectively with opposed ends of the anode and which senses the abnormality when an electrolyzing current flowing between the opposed ends of the anode lowers to less than an allowable value.

2. A leaching device for electrolyzed silver as defined in claim 1, wherein the power source control circuit comprises a detection circuit for detecting the flow of feed water or silver ion sterilized water thereby applying ON/OFF control of the electrolysis power source.

3. A leaching device for electrolyzed silver as defined in claim 1 or 2, wherein the power source control circuit comprises a constant current circuit.

4. A leaching device for electrolyzed silver as defined in claim 1 or 2, wherein the power source control circuit comprises a circuit for controlling the electrolyzing current depending on the flow rate of feed water or silver ion sterilized water.

5. A leaching device for electrolyzed silver as defined in any one of claims 1 to 2, wherein the driving circuit comprises a timer circuit for driving the polarity switching circuit on a time interval.

* * * * *